(12) United States Patent
Barrientos

(10) Patent No.: US 7,517,340 B2
(45) Date of Patent: *Apr. 14, 2009

(54) URINE COLLECTION SUSPENSION AND SAFETY SYSTEM

(75) Inventor: Joel Kwan Barrientos, 58 Sherwood Dr., Centralia, IL (US) 62801

(73) Assignee: Joel Kwan Barrientos, Centralia, IL (US)

( * ) Notice: Subject to any disclaimer, the term of this patent is extended or adjusted under 35 U.S.C. 154(b) by 1 day.

This patent is subject to a terminal disclaimer.

(21) Appl. No.: 11/342,078

(22) Filed: Jan. 27, 2006

(65) Prior Publication Data

US 2007/0179462 A1    Aug. 2, 2007

(51) Int. Cl.
*A61F 5/44* (2006.01)

(52) U.S. Cl. .................. 604/353; 604/343; 604/344; 604/345; 604/349; 604/351; 604/264; 604/523; 604/327; 604/317; 604/179; 128/876

(58) Field of Classification Search .............. 604/353, 604/343–345, 349, 351, 179, 264, 523, 327, 604/317; 128/876
See application file for complete search history.

(56) References Cited

U.S. PATENT DOCUMENTS

| | | | | |
|---|---|---|---|---|
| 2,133,130 A | | 10/1938 | Buchstein ................. 128/349 |
| 2,476,375 A | * | 7/1949 | Kent ....................... 604/353 |
| 3,726,280 A | * | 4/1973 | Lacount .................... 604/179 |
| 3,897,785 A | * | 8/1975 | Barto, Jr. .................. 604/327 |
| 4,057,066 A | * | 11/1977 | Taylor ...................... 604/180 |
| 4,073,295 A | | 2/1978 | Laufbahn ................... 128/295 |
| 4,122,851 A | * | 10/1978 | Grossner ................... 604/347 |
| 4,319,573 A | * | 3/1982 | Whitlock ................... 604/328 |
| 4,511,358 A | * | 4/1985 | Johnson et al. ............. 604/327 |
| 4,726,716 A | * | 2/1988 | McGuire ................... 604/180 |
| 5,193,553 A | * | 3/1993 | Kalinoski .................. 600/580 |
| 5,643,236 A | * | 7/1997 | Hadley ..................... 604/353 |
| 5,664,581 A | * | 9/1997 | Ashley ..................... 128/876 |
| D395,356 S | * | 6/1998 | Tang ........................ D3/327 |
| 6,096,013 A | * | 8/2000 | Hakky et al. ............... 604/349 |
| 6,645,185 B2 | * | 11/2003 | Bird et al. ................. 604/345 |

* cited by examiner

*Primary Examiner*—Ginger T. Chapman
(74) *Attorney, Agent, or Firm*—Harness, Dickey & Pierce, P.L.C.

(57) ABSTRACT

A urine collection system includes a urine collection device and a suspension system. The urine collection device includes a catheter and a urine bag. The suspension system includes a waist band, an extension strap depending from the waist band, and a thigh band attached to the strap. A pair of securing straps is provided on the thigh band for securing the urine bag. A fastener is provided on the extension strap for securing the catheter and for resisting pulling by the urine bag. The catheter further includes a branch, which, along with the fastener, resists the downward motion of the catheter.

9 Claims, 2 Drawing Sheets

URINE COLLECTION SUSPENSION AND SAFETY SYSTEM

FIELD OF THE INVENTION

The present invention relates generally to urine collection devices, and more particularly to urine collection devices with wearable supports for incontinent patients.

BACKGROUND

A conventional urine collection device includes an external or internal catheter (such as a Foley catheter) communicating with the subject's urethra, and a urine bag connected to the catheter for collecting urine. To enhance the subject's mobility the urine bag can be secured to one of the patient's thighs. The urine collection device is thus hidden under the clothing of the patient so that the patient can engage in daily activities without embarrassment.

Conventional urine collection devices, however, can cause discomfort to the patient. If not properly supported, the urine bag tends to swing back and forth across the patient's thigh as the patient moves, impeding free movement of the patient. Moreover, as more urine is collected, the weight of urine bag can cause it to slide, applying a pulling force that is at best uncomfortable for the subject, and in the case of an internal catheter, can forcibly pull the catheter from the subject's urethra, causing severe trauma and pain to the subject.

Attempts have been made to provide more secure support for urine collection device discomfort and embarrassment, and in many cases pain and trauma are still common side effects of using a mobile urine collection system.

SUMMARY

Embodiments of the present invention provide for more secure support for urine collection system with reduced risk to the user. In one preferred form, a urine bag suspension system for carrying a urine collection device is provided. The urine bag suspension system includes a waist band, a urine bag support suspended from the waist band for carrying a urine bag of the urine collection device, and a fastener. The fastener is disposed at the urine bag support for engaging the catheter of the urine collection device to resist pulling it from communication with the subject's urethra.

In another preferred form, a urine bag suspension system for carrying a urine collection device is provided. The urine collection device includes a catheter and a urine bag. The catheter has an engaging end removably engaging the urine bag. The urine bag suspension system includes a waist band, an extension strap suspended from the waist band, and a bag carrier for carrying the urine bag. The extension strap is substantially vertically suspended from the waist band and is connected to about the midway of an upper edge of the bag carrier. The bag carrier includes a pair of securing straps.

In still another preferred form, a wearable support for a urine collection system comprising a catheter and a collection bag is provided. The support comprises a waist band adapted to be worn around the user's waist, a strap depending from the waist band, and a thigh band attached to the strap, adapted to be worn around the user's thigh. The support further comprises at least one fastener on the thigh band for engaging and supporting the collection bag, and at least one fastener on the strap for engaging the catheter to resist pulling by the collection bag secured on the thigh band.

Various embodiments of the invention provide more secure support for the urine bags in urine collection systems to resist movement of the bag and attendant discomfort to the subject. Various embodiments of the invention also engage the catheter to resist movement of the catheter and resulting discomfort and trauma to the subject. Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings of preferred embodiments thereof, wherein.

Corresponding reference numerals indicate corresponding parts throughout the several views of the drawings.

DETAILED DESCRIPTION

The structure of a urine collection system in accordance with the present disclosure is now described in greater detail. The following description of the illustrated example is merely exemplary in nature and is in no way intended to limit the invention, its application, or uses.

Figure 1:
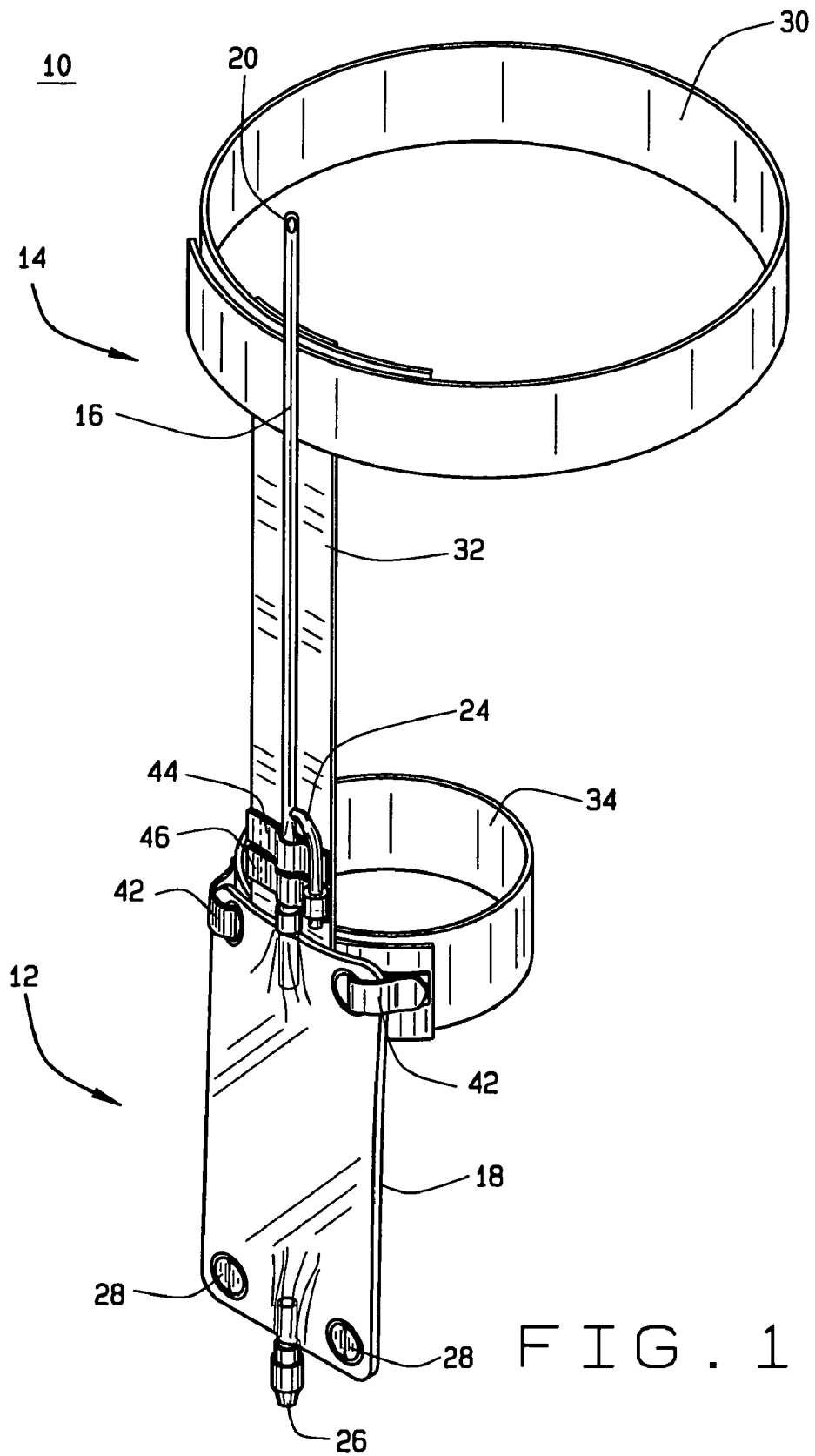
FIG. 1 is a perspective view of a urine collection system in accordance with the teachings of the present disclosure.
Figure 2:
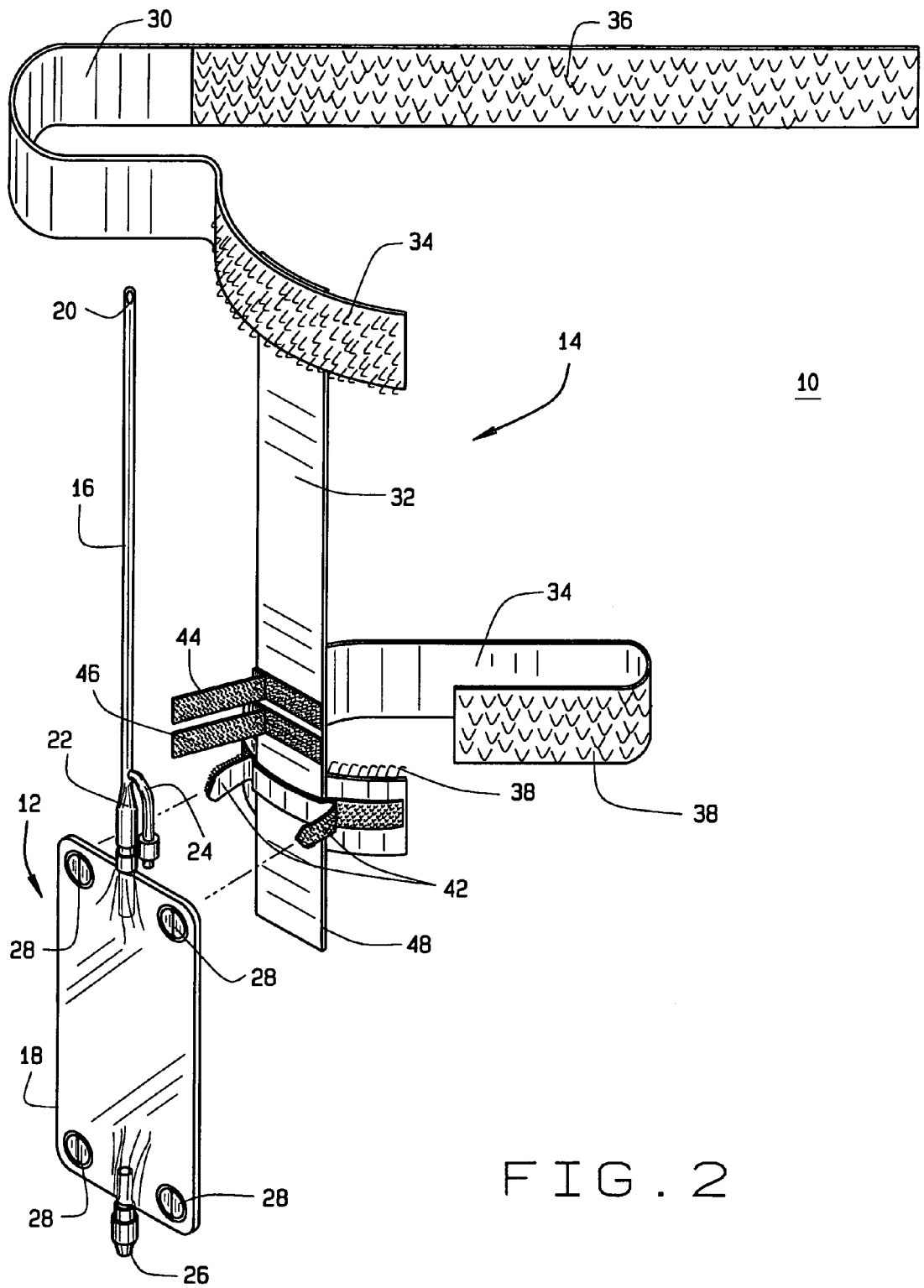
FIG. 2 is a perspective view of the urine collection system of FIG. 1, wherein the urine collection device is disassembled from a wearable suspension system therefor.

Referring to FIGS. 1 and 2, a urine collection system in accordance with the teachings of the present disclosure is illustrated and generally indicated by reference numeral 10. The urine collection system 10 includes a urine collection device 12 and a wearable support or a wearable suspension system 14. The urine collection device 12 includes a catheter 16 and a urine bag 18. The catheter 16 has an inlet end 20 for communicating with the urethra of the subject, and an outlet end 22 for engaging the urine bag 18.

The catheter 16 can be a Foley catheter, which is adapted to be inserted into the urethra of the patient, or a Texas catheter, which is to be connected to the penis of a male patient via a condom-like envelope, or any other type of internal or external urine collection catheter. In any case, the catheter 16 usually includes a branch 24 adjacent to the outlet end 22, the function of which will be described later.

The urine bag 18 has a discharge outlet 26 at the opposite end of the bag from the connection to the outlet end 22 of the catheter 16 for emptying the urine bag 24. In most applications the bag 18 is mounted generally vertically, with the connection to the outlet end 22 of the catheter at the upper end of the bag, and the discharge outlet 26 at the lower end. The urine bag 18 preferably has a generally rectangular shape with four corners and four eyelets 28, one at each of its four corners for mounting the bag.

The suspension system 14 is used to support and carry the urine collection device 12 on the subject, and includes a waist band 30, an extension strap 32 depending from the waist band 30, and a thigh band 34 attached adjacent the free end of the extension strap 32. The waist band 30 could be a continuous loop, but it is preferably in the form of a belt for encircling the entire waist of the subject. The waist band 30 could also be in the form of a strip to be attached to a piece of clothing around the subject's waist without completely encircling the subject's waist. In either case, the waist band 30 can be provided with a fastener 36 to make it easy for the subject to put the suspension system 14 on, and take it off. In the illustrated example, the fastener 36 includes an elongated band with mating fastener elements. The mating fastening elements are preferably mating patches of a hook-and-loop style fastener, such as Velcro® fastener, to allow easy attachment and detachment. However, any conventional fasteners, such as buckles, buttons, or snaps, could be used for securing the waist band 30 around the subject's waist or to the subject's clothing could be used without departing from the spirit of the present disclosure.

The thigh band 34 is generally parallel to the waist band 30 and is sufficiently long to surround the subject's thigh. The thigh band 34 could be a continuous loop, but it is preferably in the form of a belt a belt for encircling the entire thigh of the subject, The thigh band 34 can be provided with a fastener 38 to make it easy for the subject to put the suspension system 14 on, and take it off. In the illustrated example, the fastener 38 includes an elongated band with mating fastener elements. The mating fastening elements 38 are preferably mating patches of a hook-and-loop style fastener, such as Velcro®) fastener, to allow easy attachment and detachment. However, any conventional fasteners, such as buckles, buttons, or snaps, could be used for securing the thigh band 34 around the subject's thigh could be used without departing from the spirit of the present disclosure.

A pair of securing straps 42 is provided on the thigh band 34 adjacent to the extension strap 32. The securing straps 42 are positioned to engage an adjacent opening 28 at the top corners of the urine bag 18 to secure the urine bag 18 on the thigh band 34. It should be noted that while the securing straps 42 are shown to be provided on the thigh band 34 in the illustrated example, the securing straps 42 can be provided on the extension strap 32, instead of thigh band 34, as long as the securing straps 42 can be positioned to engage the adjacent openings 28 of the urine bag 18 to secure the urine bag 18 to the suspension system 14. Because the thigh band generally does not change in dimension, the corners of the bag 18 are held in a substantially fixed distance, preventing crushing of the bag, which could tend to apply a back pressure to the catheter.

The extension strap 32 extends perpendicularly from the waist band 30 a sufficient length so that when the waist band is secured at the subject's wait, the strap extends down along the side of the subject sufficiently such that the thigh band 34 can be attached to the thigh of the subject. A pair of fasteners 44 and 46 are disposed at the extension strap 32 for positioning and securing the catheter 16. The fasteners 44 and 46 are disposed adjacent to the outlet end 22 and below the branch 24. The branch 24 provides for attachment to a pump device, which can be used to inflate a balloon that may be disposed at the end of the catheter 16 for anchoring the catheter within the subject's urethra. The engagement between the fasteners 44 and the branch 24 resists movement of, the catheter 16 due to pulling of the bag from movement by the subject or from the increasing weight of urine that is collected in the bag. Therefore, the catheter 16 remains in a "slack" or "no tension" state despite the increased weight of the urine bag 18 and no pulling force is exerted on the urethra of the patient to cause pain. The fasteners 44 and 46 include fastening means, such as mating patches of a hook-and-loop style fastener, Velcro®, although some other type of fastening means could be used.

A panel 48 is provided at a lower end of the extension strap 32 to separate and insulate the patient's thigh from the urine bag 18. The panel 48 can be of any shape and size and does not have to be an integral part of the extension strap 32 as shown in the illustrated example, as long as the panel 48 provides proper separation between the urine bag 18 and the thigh to improve comfort. The panel 48 can be of sufficient size and length so that a second pair of securing straps or a second thigh band can be attached to the panel 48 to secure the lower end of the urine bag 18. Alternatively, the panel 48 can be in a form of a pouch to receive the urine bag 18 therein.

The waist band 30 and the extension strap 32 are preferably made of a washable, non-stretchable material so that the construction of the suspension system 14 is not distorted due to the increased weight of the urine bag 18.

With the construction of the present urine collection system 10, the urine collection device 12 can be easily disassembled from the suspension system 14 for cleaning or emptying purposes.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A urine bag suspension system for carrying a urine collection device including a catheter and a urine bag, the catheter having an engaging outlet end removably engaging the urine bag, and a branch depending therefrom providing for attachment of the branch to a pump device, the urine bag suspension system comprising:
   a waist band;
   a urine bag support suspended from the waist band for carrying a urine bag, wherein the urine bag support comprises an extension strap and a thigh band attached to the extension strap, the thigh band being positioned on the extension strap relative to the waist band so as to wrap around the thigh of a patient;
   a pair of securing straps attached to the thigh band and the extension strap, each securing strap comprising a fastener portion that is configured to be received through an opening in a top corner of a urine collection bag, and to engage a mating portion on the thigh band, to thereby secure the urine bag to the suspension system; and
   a first fastener positioned on the extension strap above the thigh band, the first fastener being configured to engage the catheter below the branch only, to secure the catheter without securing the branch such that the first fastener resists downward movement of the catheter and provides for attachment of the branch to a pump device;
   a second fastener positioned on the extension strap above the thigh band and below the first fastener, the second fastener being configured to engage the catheter above the outlet end of the catheter and below the branch of the catheter;
   whereby the urine bag suspension system is free of fasteners above the branch in the catheter, such that disengaging the first and second fasteners positioned below the branch provides for disassembly of the suspension system from the catheter for cleaning purposes.

2. The urine bag suspension system according to claim 1, wherein the first fastener and a second fasteners maintain the engaging outlet end of the catheter in place when the engaging outlet end disengages from the urine bag.

3. The urine bag suspension system according to claim 1, wherein the urine bag support is configured so that the engaging end of the catheter extends in a direction substantially vertical to the waist band when the urine bag is carried by the urine bag support.

4. The urine bag suspension system according to claim 1, wherein the urine bag support comprises an extension strap and a thigh band attached to the extension strap that includes mating hook and loop style fasteners.

5. The urine bag suspension system according to claim 4, wherein the extension strap is substantially vertically suspended from the waist band.

6. The urine bag suspension system according to claim 4, wherein the extension strap is made of a non-stretchable material.

7. The urine bag suspension system according to claim 4, wherein the thigh band is positioned below the first and second fasteners.

8. The urine bag suspension system according to claim 1, wherein the urine bag support further comprises a panel for separating the urine bag from a thigh of a patient.

9. A urine bag suspension system for carrying a urine collection device including a catheter and a urine bag, the catheter having an engaging outlet end removably engaging the urine bag, and a branch depending therefrom providing for attachment of the branch to a pump device, the urine bag suspension system comprising:
 a urine bag;
 a waist band;
 a urine bag support suspended from the waist band for carrying the urine bag, wherein the urine bag support comprises an extension strap and a thigh band attached to the extension strap the thigh band being positioned on the extension strap relative to the waist band so as to wrap around the thigh of a patient;
 a pair of securing strap attached to the thigh band and the extension strap each securing strap comprising a fastener portion that is configured to be received through an opening in a top corner of a urine collection bag, and to engage a mating portion on the thigh band, to thereby secure the urine bag to the suspension system;
 a catheter having an engaging outlet end removably engaging the urine bag, and a branch depending therefrom that provides for attachment of a pump device thereto; and
 a first fastener positioned on the extension strap above the thigh band, the first extension strap being configured to engage the catheter below the branch only, to secure the catheter without securing the branch such that the first fastener resists downward movement of the catheter and provides for attachment of the branch to a pump device;
 a second fastener positioned on the extension strap above the thigh band and below the first fastener, the second fastener being configured to engage the catheter above the outlet end of the catheter and below the branch of the catheter;
 whereby the urine bag suspension system is free of fasteners above the branch in the catheter, such that disengaging the first and second fasteners positioned below the branch provides for disassembly of the suspension system from the catheter for cleaning purposes.

* * * * *